United States Patent [19]

Smith, Jr.

[11] 4,059,634

[45] Nov. 22, 1977

[54] PRODUCTION OF PINACOLONE

[75] Inventor: Donovan Norman Smith, Jr., Kansas City, Mo.

[73] Assignee: Mobay Chemical Corporation, Pittsburgh, Pa.

[21] Appl. No.: 640,828

[22] Filed: Dec. 15, 1975

[51] Int. Cl.$^2$ .............................................. C07C 45/00
[52] U.S. Cl. ................................................ 260/593 R
[58] Field of Search ......................... 260/593 R, 340.7

[56] References Cited

U.S. PATENT DOCUMENTS

| 2,307,894 | 1/1943 | Mikeska | 260/340.7 |
| 3,062,835 | 11/1962 | Signorino | 260/340.7 |

FOREIGN PATENT DOCUMENTS

| 714,488 | 12/1941 | Germany | 260/593 R |
| 143,028 | 5/1961 | U.S.S.R. | 260/593 R |
| 144,167 | 2/1962 | U.S.S.R. | 260/593 R |

OTHER PUBLICATIONS

Safarov et al., Chem. Abst., vol. 78, p. 408, (1973).
Nishimura et al., Chem. Abst., vol. 61, (1967).

Primary Examiner—James O. Thomas, Jr.
Assistant Examiner—James H. Reamer
Attorney, Agent, or Firm—Burgess, Dinklage & Sprung

[57] ABSTRACT

In the process wherein 4,4,5-trimethyl-1,3-dioxane is contacted with aqueous acid to produce pinacolone, the improvement which comprises effecting the contact in the presence of 2-methyl-but-2-ene, whereby the yield of pinacolone is increased. Advantageously the 2-methyl-but-2-ene is present in approximately equimolar amount with the 4,4,5-trimethyl-1,3-dioxane and the acid is HCl of about 30 to 40% concentration or HBr of about 30 to 50% concentration.

6 Claims, No Drawings

PRODUCTION OF PINACOLONE

The present invention relates to a process for the preparation of pinacolone. This compound is useful as a solvent and as a starting material for further syntheses, for example for the preparation of known herbicidally active substances.

It has already long been known that pinacolone (2,2-dimethyl-3-oxo-butane) can be prepared from pinacol (2,3-dimethylbutane-2,3-diol) by treatment with dilute sulfuric acid (the "pinacol-pinacolone rearrangement"; see, for example, Beilsteins Handbuch der Organischen Chemie (Handbook of Organic Chemistry), 4th edition, volume I, page 694). However, this process has the great disadvantage that it is difficult to carry out on a large scale.

In order to obtain pinacol, acetone (I) is reduced with aluminum filings, mercury (II) chloride being added as an activator (see Beilstein, Supplementary Volume I, page 252):

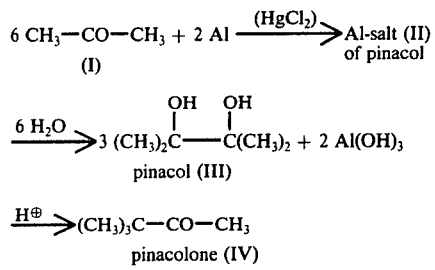

The particular disadvantage of this preparative method is that aluminum, which is expensive, is required as a starting material and that, based on aluminum, only yields of pinacolone which do not exceed 50–60% of theory are obtained. Since acetone is employed in a large excess and can be recovered in the pure form only with difficulty, the yield is even poorer when it is based on the consumption of acetone.

A further disadvantage of this process is that toxic mercury (II) chloride is required as the activator and the major part of this is converted into elementary mercury during the reaction. Despite working in a careful manner it is never possible quantitatively to isolate the mercury employed, so that considerable amounts of mercury pass into the effluent and into the outgoing air.

The fact that at the same time considerable amounts of aluminum salts are obtained, the separation of which as an aqueous solution or as solid aluminum hydroxide is associated with great difficulties and usually with loss of material, is to be regarded as a further disadvantage of this process. Even after they have been separated off, the aluminum salts cause problems because they cannot be further used and pass either into the effluent or to a dump.

The reaction is very highly exothermic and extremely vigorous and this is to be regarded as a further disadvantage of the known process. The reaction therefore requires special precautions, especially because it can be carried out only with absolutely dry starting materials. If the starting material is moist, the reaction either does not start at all or starts delayed, in an uncontrollable manner.

Moreover, a disadvantage of the synthesis of pinacolone via pinacol, which has been prepared by reduction of acetone, is that a total of three reaction stages are required:

1. Reduction of acetone with aluminum,
2. Hydrolysis of the aluminum salt of pinacol with water, and
3. Rearrangement of pinacol to give pinacolone.

It is also known that pinacolone is obtained when 4,4,5-trimethyl-1,3-dioxane (VI) is treated at the boil with acids, preferably dilute inorganic acids and also strong organic acids (see German Patent Specification No. 714,488). 4,4,5-Trimethyl-1,3-dioxane can be prepared easily in an approximately 80% yield by reacting aqueous formaldehyde with 2-methyl-but-2-ene (V) in the presence of acids (see Houben-Weyl-Muller, Methoden der Organischen Chemie (Methods of Organic Chemistry), Volume 6/3, page 266 et seq.):

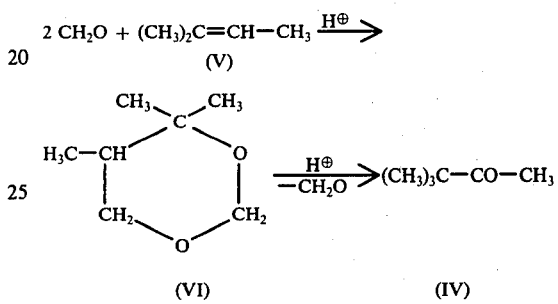

According to the data given in German Patent Specification No. 714,488, it is not possible to force a reasonably complete conversion of 4,4,5-trimethyl-1,3-dioxane (VI) to pinacolone. In Example 1 of this patent specification the conversion is, for example, only 76.7%. Thus, the pinacolone formed is always contaminated with relatively large amounts of starting material, which has to be separated off by an additional process step. This is also necessary because, for economic reasons, the valuable starting material has to be re-used, after it has been separated off, for the preparation of pinacolone.

A further disadvantage is that a total of 2 moles of formaldehyde is required in order to prepare 1 mole of 4,4,5-trimethyl-1,3-dioxane (VI); 1 mole of this formaldehyde is liberated again during the subsequent splitting with acid and is thus lost and finally passes into the effluent, which thus has a very high oxygen demand for chemical or biological degradation.

However, a particular disadvantage of this method of preparation is the fact that only low yields are achieved. Thus, the maximum yield according to Example 1 of the patent specification mentioned is only 43.3% of theory, based on 4,4,5-trimethyl-1,3-dioxane employed, or 56.5% of theory, based on the conversion. This results, inter alia, in a considerable amount of by-products being obtained in the form of a viscous oil, which, when the reaction is carried out on an industrial scale, can be disposed of only by combustion.

The present invention provides a process for the preparation of pinacolone, which has the formula $$(CH_3)_3C-CO-CH_3 \qquad (IV)$$

in which 4,4,5-trimethyl-1,3-dioxane is contacted with aqueous acid to produce pinacolone, the contact being effected in the presence of 2-methyl-but-2-ene, whereby the yield of pinacolone is increased.

The reaction scheme can be illustrated as follows:

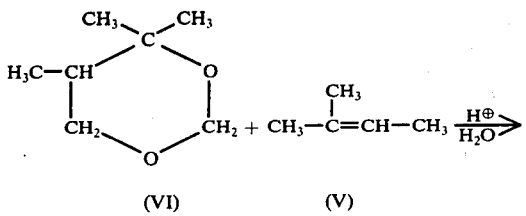

(VI)    (V)

$$2\ CH_3-\underset{\underset{CH_3}{|}}{\overset{\overset{CH_3}{|}}{C}}-\overset{\overset{O}{\|}}{C}-CH_3$$

(IV)

Advantageously, the 2-methyl-but-2-ene is present in approximately equimolar amount with the 4,4,5-trimethyl-1,3-dioxane, and the acid is a hydrogen halide of about 30 to 50% concentration, especially about 30 to 40% HCl or 30 to 50% HBr. The reaction temperature can be varied widely but for speed of reaction an elevated temperature of at least about 60° C is desirable. The temperature is desirably about 80° C, but it can even be higher, i.e. up to the boil which commences at about 98° C at atmospheric pressure or higher if the reaction vessel is pressurized, possibly as high as 20 bars, although this is not necessary.

It is to be regarded as extremely surprising that, according to the reaction of the invention, pinacolone can be prepared in such high yield, the amount of formaldehyde required even theoretically being only half that required by the prior art. According to the process of the invention, yields of up to about 75% of theory can be achieved. According to the state of the art, yields of at most 45.2% of theory (based on an 80% yield of the 2-methyl-butene (V) to 4,4,5-trimethyl-1,3-dioxane (VI) and a yield of pinacolone (IV) of at most 56.5% of theory (VI). Based on trimethyl-dioxane as the reactant, the yield to pinacolone is almost 70%.

The process according to the invention has a number of advantages. Thus, it avoids all the disadvantages which are associated with the best process according to the state of the art, that is the reductive dimerization of acetone by means of aluminum to give pinacol and the subsequent rearrangement of this by means of sulfuric acid to give pinacolone.

Furthermore, the process according to the invention makes it possible for the first time to prepare the valuable intermediate product pinacolone in an economic manner from the ultimate raw materials 2-methyl-but-2-ene and formaldehyde, since it is possible with the aid of the process according to the invention to carry out the reaction with high yields and at the same time to reduce the consumption of formalin to half and to obtain pinacolone. In addition the high yields reduce the amount of by-products and waste materials which are necessarily obtained and make the process less harmful to the environment than the processes of the prior art.

Possible diluents, in addition to water, are all inert solvents, especially hydrocarbons, such as pentane or hexane, and ketones, such as, for example, pinacolone. However, the use of solvents has no advantages for the reaction according to the invention, although it is unavoidable when the starting materials trimethyl-dioxane and/or 2-methyl-but-2-ene are not pure but also contain other hydrocarbons.

While the hydrogen halides are preferred, sulfuric or phosphoric acids of 20-60% concentration can also be employed.

It is also essential for the reaction according to the invention that provision is made for intensive mixing of the reaction mixture during the reaction and the subsequent reaction. This can be effected by using suitable stirrers and appropriate speeds of rotation of the stirrers but optionally also by adding small amounts of an emulsifier to the reaction mixture.

When the reaction is complete, and optionally after neutralization of the inorganic acid, pinacolone is distilled off azeotropically together with water from the reaction mixture, the distillation preferably being effected via a column in order to achieve a higher purity of the pinacolone. However, it is also possible to separate the two phases after the reaction is complete and to use all or part of the aqueous phase as aqueous inorganic acid for a renewed reaction. The organic phase which is separated off contains the pinacolone, which in this case also is isolated and purified most appropriately by distillation.

According to a particular embodiment, the reaction according to the invention can also be carried out continuously, preferably by using a reaction cascade and a distillation column which operates continously.

Pinacolone can be used, for example, as an intermediate for the synthesis of known herbicidally active substances. In the following text the synthesis of 6-tert.-butyl-3-methylthio-4-amino-1,2,4-triazin-5)4H)-one (X), a compound having a herbicidal action, is described as an example (see U.S. Pat. No. 3,671,523).

1st Stage

Pinacolone is converted according to a process known from the literature by oxidation with potassium permanganate into trimethylpyruvic acid [(CH₃)₃C—CO—COOH] (compare Monatshefte fur Chemie, Volume 10 (1889), page 771).

2nd Stage

Analogously to instructions given by A. Dornow and others (Chem. Berichte 97 (1964), page 2173–2178), 53 g (0.5 mole) of thiocarbohydrazide are dissolved in 500 ml of boiling water and 65 g (0.5 mole) of trimethylpyruvic acid are added slowly. A colorless precipitate is deposited, which is filtered off, washed with water and dried in vacuo at 50° C. 6-tert.-butyl-3-mercapto-4-amino-1,2,4-triazin-5(4H)-one is obtained from this reaction in almost quantitative yield.

3rd Stage 4 parts by weight of 6-tert.-butyl-3-mercapto-4-amino-1,2,4-triazin-5(4H)-one are dissolved in a mixture of 11 parts by weight of 2-normal sodium hydroxide and 4 parts by weight of methanol and the solution is treated at 0° C with 3.2 parts by weight of methyl iodide. The reaction mixture is then stirred for a further 4 hours at 20° C. The reaction product crystallizes out and is filtered off, dried and recrystallized from benzene. 3.52 parts by weight of 6-tert.-butyl-3-methylthio-4-amino-1,2,4-triazin-5(4H)-one of melting point 126°–127° C are obtained Yield: 82% of theory.

The process of this invention is illustrated by the following preparative examples.

EXAMPLE 1

In a 1 liter Morton flask fitted with a high speed stirrer, thermometer, dropping funnel and brine condenser was placed 270 ml of 36% HCl. The acid was heated to 80° C and a mixture of 148.9 grams of 87.3% (4,4,5-trimethyl-1,3-dioxane, 1.0 mole) and 80.0 grams of 87.5% 2-methyl-but-2-ene (2-MB-2, 1.0 mole) was added dropwise over a period of 12 hours while keeping the flask at 80°–85° C. The mixture was then stirred at 80°–85° C for a further 30 minutes at which time a GLC scan indicated essentially all of the trimethyl-dioxane had been consumed. After neutralization of the reaction mixture with 50% NaOH the flask was adapted for distillation and the material boiling up to 100° C was collected and analyzed for pinacolone content. The organic residue in the flask was also weighed. The results are set forth in the Table.

In the Table, the yields based on formaldehyde and 2-methyl-but-2-ene include the amounts of these materials consumed in forming the trimethyl-dioxane starting material, such reaction being described in Houben-Weyl, supra, and involving about an 80% yield of trimethyl-dioxane based on 2-methyl-but-2-ene but a somewhat lower yield based on formaldehyde.

EXAMPLES 2–10

The procedure of Example 1 was repeated with variations in the conditions. The results obtained are also set forth in the Table.

COMPARISON EXAMPLE

The process of Example 1 was repeated except that the 1 mole of 2-methyl-but-2-ene was replaced by 1 mole of its condensation product with formaldehyde, viz. 4,4,5-trimethyl-1,3-dioxane. Thus, 2 moles of the trimethyl-dioxane were reacted. As shown in the Table, the yields on all bases are markedly lower than in Example 1. The distillation residue, i.e. materials boiling above 100° C, was almost 5 times as great as in Example 1. The concentration of pinacolone in the distillate is somewhat higher than in Example 1, indicating the by-products in the comparison are higher boiling compared with the lower boiling by-products in Example 1.

TABLE

PREPARATION OF PINACOLONE FROM 4,4,5-TRIMETHYL-1,3-DIOXANE AND 2,METHYL-BUT-2-ENE

| EXAMPLE | ACID NAME | ACID CONC. | ACID ml | ADDING TIME, HRS. | POSE HEATING TIME, HRS. | DISTILLATE, gms | RESIDUE, gms | % YIELD, BASED ON TMD | % YIELD, BASED ON $CH_2O$ | % YIELD, BASED ON 2-MB-2 |
|---|---|---|---|---|---|---|---|---|---|---|
| 1 | HCl | 36 | 270 | 12 | 0.5 | 190 | 27.6 | 69.0 | 50.6 | 59.1 |
| 2 | HCl | 10 | 270 | 13 | 0.5 | 124.9 | 36.8 | 32.6 | 23.9 | 27.9 |
| 3 | HCl | 20 | 270 | 12 | 0.5 | 157.7 | 40.3 | 57.5 | 42.1 | 49.2 |
| 4 | HCl | 36 | 270 | 12 | 2.0 | 179.3 | 31.8 | 66.9 | 49.0 | 57.3 |
| 5* | HCl | 36 | 270 | 12 | 0.5 | 175.9 | 38.7 | 63.1 | 46.2 | 54.0 |
| 6 | HCl | 36 | 270 | 6 | 2.0 | 177.2 | 49.4 | 62.5 | 45.8 | 53.4 |
| 7 | HCl | 36 | 135 | 6 | 2.3 | 153.7 | 53.9 | 53.3 | 39.1 | 45.6 |
| 8 | HCl | 36 | 405 | 6 | 1.5 | 185.7 | 35.1 | 65.3 | 47.9 | 55.8 |
| 9 | HBr | 48 | 270 | 12 | 3.0 | 188.6 | 26.0 | 66.2 | 48.5 | 56.7 |
| 10 | $H_2SO_4$ | 36 | 270 | 12 | 4.0 | 126.9 | 76.2 | 47.4 | 39.7 | 40.6 |
| COMPARISON** | HCl | 36 | 270 | 12 | 0.5 | 124.9 | 127.2 | 47.5 | 17.4 | 40.7 |

*5 gms emulsifier added.
**In place of 1 mole of 2-MB-2, a second mole of TMD was added.

It will be appreciated that the instant specification and claims are set forth by way of illustration and not limitation, and that various modifications and changes may be made without departing from the spirit and scope of the present invention.

What is claimed is:

1. In the process wherein 4,4,5-trimethyl-1,3-dioxane is contacted with aqueous acid to produce pinacolone, the improvement which comprises slowly adding the 4,4,5-trimethyl-1,3-dioxane and approximately an equimolar amount of 2-methyl-but-2-ene to stirred aqueous hydrogen halide acid having a concentration of about 20 to 60%, whereby the yield of pinacolone is increased.

2. The process according to claim 1, wherein the aqueous acid is a hydrogen halide of about 30 to 50% concentration.

3. The process according to claim 1, wherein contact is effected at a temperature of about 60° C up to the boil.

4. The process according to claim 3, wherein the aqueous acid is a hydrogen halide of about 30 to 50% concentration and contact is effected at a temperature of about 60° C up to the boil, the mixture thereafter being neutralized and then distilled to remove pinacolone.

5. The process according to claim 4, wherein the aqueous acid is hydrogen chloride of about 30 to 40% concentration.

6. The process according to claim 4, wherein the aqueous acid is hydrogen bromide.

* * * * *